US012357754B2

(12) United States Patent
Lee et al.

(10) Patent No.: US 12,357,754 B2
(45) Date of Patent: Jul. 15, 2025

(54) THERMAL FLOW METER FOR ELECTRIC DRUG INJECTION PUMP AND METHOD FOR MEASURING FLOW USING SAME

(71) Applicant: KOREA INSTITUTE OF MACHINERY & MATERIALS, Daejeon (KR)

(72) Inventors: Dongkyu Lee, Daegu (KR); Ohwon Kwon, Daegu (KR); Changwon Kim, Daegu (KR); Kang-Ho Lee, Daegu (KR); Jiae Kim, Daegu (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 721 days.

(21) Appl. No.: 17/432,388

(22) PCT Filed: Jan. 30, 2020

(86) PCT No.: PCT/KR2020/001427
§ 371 (c)(1),
(2) Date: Aug. 19, 2021

(87) PCT Pub. No.: WO2020/171413
PCT Pub. Date: Aug. 27, 2020

(65) Prior Publication Data
US 2022/0184301 A1    Jun. 16, 2022

(30) Foreign Application Priority Data

Feb. 22, 2019   (KR) .......................... 10-2019-0021330

(51) Int. Cl.
*A61M 5/168* (2006.01)

(52) U.S. Cl.
CPC . *A61M 5/16886* (2013.01); *A61M 2205/3334* (2013.01); *A61M 2205/3368* (2013.01); *A61M 2205/36* (2013.01)

(58) Field of Classification Search
CPC ...... A61M 5/16886; A61M 2205/3334; A61M 2205/3368; A61M 2205/36; G01F 1/684; G01F 1/6847; G01F 1/6842
See application file for complete search history.

(56) References Cited

U.S. PATENT DOCUMENTS

| 4,384,578 A | * | 5/1983 | Winkler | ............ | A61M 5/16886 |
|---|---|---|---|---|---|
| | | | | | 73/204.22 |
| 4,938,079 A | | 7/1990 | Goldberg | | |

FOREIGN PATENT DOCUMENTS

| JP | 11-351930 A | 12/1999 | | |
|---|---|---|---|---|
| JP | 4962489 B2 | * 6/2012 | ........... | G01F 1/6845 |

(Continued)

OTHER PUBLICATIONS

International Search Report issued on May 14, 2020 for corresponding international application No. PCT/KR2020/001427.

(Continued)

*Primary Examiner* — Timothy P Graves
(74) *Attorney, Agent, or Firm* — Hauptman Ham, LLP

(57) ABSTRACT

In a flow meter for an electric drug injection pump and a method for measuring a flow using the flow meter, the flow meter includes a lower case, an upper case and a temperature sensor part. A plurality of grooves and an extending groove are formed in the lower case. The grooves are spaced apart from each other. The extending groove extends along the grooves and a tube is positioned in the extending groove. The upper case faces the lower case and is combined with the lower case, to fix the tube. The heater is positioned at one of the grooves, to supply a heat to a fluid passing through the tube. The temperature sensor part is positioned at each of the (Continued)

grooves, to measure the temperature of the fluid passing through the tube. The tube is positioned to make contact with the heater and the temperature sensor part.

16 Claims, 9 Drawing Sheets

(56) References Cited

FOREIGN PATENT DOCUMENTS

| KR | 10-1682145 B1 | 12/2016 | | |
|---|---|---|---|---|
| KR | 101824866 B1 | * | 2/2018 | ............ G01F 1/684 |
| KR | 10-2018-0088136 A | | 8/2018 | |
| KR | 20180088136 A | * | 8/2018 | ............ G01F 1/684 |

OTHER PUBLICATIONS

Written Opinion issued for corresponding International Patent Application No. PCT/KR2020/001427 on May 14, 2020.

* cited by examiner

THERMAL FLOW METER FOR ELECTRIC DRUG INJECTION PUMP AND METHOD FOR MEASURING FLOW USING SAME

CROSS-REFERENCE TO RELATED APPLICATION

The present application is a national stage filing under 35 U.S.C § 371 of PCT application number PCT/KR2020/001427 filed on Jan. 30, 2020 which is based upon and claims the benefit of priorities to Korean Patent Application No. 10-2019-0021330, filed on Feb. 22, 2019, in the Korean Intellectual Property Office. Both of the aforementioned applications are hereby incorporated by reference in their entireties.

BACKGROUND

1. Field of Disclosure

The present disclosure of invention relates to a flow meter for an electric drug injection pump and a method for measuring a flow using the flow meter, and more specifically the present disclosure of inventions relates to a flow meter for an electric drug injection pump and a method for measuring a flow using the flow meter, by which a flow rate or a flow velocity of a fluid such as a drug passing through an electric drug injection pump is measured using a temperature sensor part without making direct contact with the drug in a relatively larger area, more precisely and more accurately.

2. Description of Related Technology

As for a recently developed and used electric drug injection pump, an indirect type flow rate measuring device in which the flow rate of an injected drug is calculated by rotating an axis of CAM is normally used. However, in the indirect type flow rate measuring device, an error is increased in the measuring and stability in injecting the drug is decreased. In addition, FDA (Food and Drug Administration) requires that the measuring technology for directly or indirectly measuring an actual injection flow rate should be equipped in the electric drug injection pump, and thus the technology for measuring the flow rate of the electric drug injection pump more accurately should be developed.

However, many technical barriers should be solved to develop the measuring technology in the electric drug injection pump. For example, the measuring device should be performed without making direct contact with the drug, an injection tube line should be commonly used and a sensor should be re-used. In addition, since a painkiller is injected with a relatively lower flow rate about 2 mL/hr, the technology of measuring the relatively lower flow rate more precisely and more accurately is necessary.

However, until now, a flow meter having the performance mentioned above has not been developed, and Korean patent No. 10-1682145 merely discloses the technology measuring an accurate and precise flow rate using a heat signal even though the technology is not related to the flow meter measuring the flow rate.

In the above technology measuring the flow rate using the heat signal, a measuring period or a sensitivity may be changed a lot according to a heat transferring state at each measuring circumstance. Thus, the sensor should be arranged to make direct contact with the fluid. Further, the above technology is rarely related to the flow meter measuring the flow rate of the drug, and thus the un-contact type device in which the drug and the sensor do not make contact with each other may be hardly manufactured in the above technology.

Related prior art is Korean patent No. 10-1682145.

SUMMARY

The present invention is developed to solve the above-mentioned problems of the related arts. The present invention provides a flow meter for an electric drug injection pump, capable of measuring the flow rate in a relatively larger area, more precisely and more accurately, without making direct contact with a drug.

In addition, the present invention also provides a method for measuring a flow using the flow meter.

According to an example embodiment, the flow meter includes a lower case, an upper case and a temperature sensor part. A plurality of grooves and an extending groove are formed in the lower case. The grooves are spaced apart from each other. The extending groove extends along the grooves and a tube is positioned in the extending groove. The upper case faces the lower case and is combined with the lower case, to fix the tube. The heater is positioned at one of the grooves, to supply a heat to a fluid passing through the tube. The temperature sensor part is positioned at each of the grooves, to measure the temperature of the fluid passing through the tube. The tube is positioned to make contact with the heater and the temperature sensor part.

In an example, the upper case may include a plurality of pressing parts respectively arranged with the grooves, and the pressing parts may press the tube to be tightly attached to the heater and the temperature sensor part.

In an example, the flow meter may further include a plurality of supporting parts disposed at the grooves respectively, to support the pressing parts respectively.

In an example, the grooves may include first, second and third grooves which are sequentially disposed along a direction of a fluid passing through the tube.

In an example, a first temperature sensor may be disposed at the first groove, second and third temperature sensors and the heater may be disposed at the second groove, and a fourth temperature sensor may be disposed at the third groove.

In an example, the heater may be disposed between the second temperature sensor and the third temperature sensor.

In an example, the first temperature sensor may measure an initial temperature of the fluid flowing into the tube, and the fourth temperature sensor may measure a temperature of the fluid heated by the heater and flowing out of the tube.

In an example, the second temperature sensor may measure decrease of the temperature of the heater as the fluid passes through the heater, and the third temperature sensor may measure decrease of the temperature of the heater as the fluid passes through the heater and measure the temperature of the fluid heated by the heater.

According to another example embodiment, in the method for measuring flow, an initial value of flow of a fluid passing through a temperature sensor part and a tube is determined. The fluid is supplied to the tube. A flow direction of the fluid passing through the tube, is recognized based on a temperature measured by the temperature sensor part. An applied equation for measuring the flow of the fluid, is decided based on the temperature measured by the temperature sensor part. The flow is determined based on the applied equation.

In an example, the temperature sensor part may include first, second, third and fourth temperature sensors, and the initial value of each of the first to fourth temperature sensors and the initial value of the flow of the fluid may be determined to be zero.

In an example, in the recognizing the flow direction of the fluid, the flow direction of the fluid may be recognized by the temperature measured by the second and third temperature sensors respectively disposed at both sides of the heater.

In an example, in the deciding the applied equation, the applied equation may be decided based on a range of a first comparison value which is a difference between a first temperature difference and a second temperature difference. The first temperature difference may be a difference between the temperature measured by the fourth temperature sensor and the temperature measured by the second temperature sensor. The second temperature difference may be a difference between the temperature measured by the second temperature sensor and the temperature measured by the first temperature sensor.

In an example, in the determining the flow, the flow may be proportional to the first comparison value when the first comparison value is less than 10° C., and the flow may have a logarithmic relationship with the first comparison value when the first comparison value is between 10° C. and 16° C.

In an example, in the determining the flow, the flow may have an exponential relationship with a second comparison value when the first comparison value is between 16° C. and 21° C. The second comparison may be a difference between a third temperature difference and a fourth temperature difference. The third temperature difference may be a difference between the temperature measured by the fourth temperature sensor and the temperature measured by the third temperature sensor. The fourth temperature difference may be a difference between the temperature measured by the third temperature sensor and the temperature measured by the first temperature sensor.

In an example, in the determining the flow, the flow may have a logarithmic relationship with a third comparison value when the first comparison value is over 21° C. The third comparison value may be the sum of a fifth temperature difference and the second temperature difference. The fifth temperature difference may be a difference between the temperature measured by the fourth temperature sensor and the temperature measured by the first temperature sensor.

According to the present example embodiments, in the conventional heat-based flow rate measuring device, the sensor makes direct contact with the fluid. However, in the present example embodiments, the temperature sensor part and the heater are disposed on an outer surface of the tube through which the fluid passes, so that the sensor does not make direct contact with the fluid and the flow rate may be precisely and accurately measured.

Here, the tube may be a fixed type or may be inserted or detached from the extending groove, so that the flow rate of the fluid passing through various kinds of tubes may be selectively measured if necessary. Thus, user's usability and convenience may be more increased.

Since the temperature sensor part and the heater are disposed on the outer surface of the tube, a pressing part is additionally equipped to pressurize the tube to the temperature sensor part and the heater. Thus, the heating effect to the fluid and the measuring accuracy may be more increased.

Here, the temperature sensor part includes four temperature sensors, and the sensors are separately disposed at the plurality of grooves spaced apart from each other. Thus, the sensing information from each sensor may be separated and the temperature may be measured more accurately and more precisely.

For example, the second temperature sensor and the third temperature sensor are disposed at both sides of the heater, and separately measure the decreasing temperature of the heater when the fluid passes through, or the temperature of the fluid heated in the heater. Thus, the changes of the temperatures at various kinds of drug injection circumstances may be precisely and accurately detected, with the first temperature sensor measuring the reference temperature and the fourth temperature sensor measuring the temperature increasing. Further, when the flow rate is relatively lower, the above measuring may be more effective.

The above technology may be confirmed using an actual flow rate measuring method, and based on the difference of the temperatures measured by four temperature sensors, the relationship between the flow rate and the temperature may be obtained merely by using a proportional relationship or a log function relationship (or exponential function relationship). Thus, the flow rate may be detected more accurately and precisely.

For both of a range of relatively lower flow rate and a range of relatively higher flow rate, for example in the range of the flow rate between 0 mL/hr and 100 mL/hr, the precise and accurate flow rate may be detected or measured.

Figure 1:
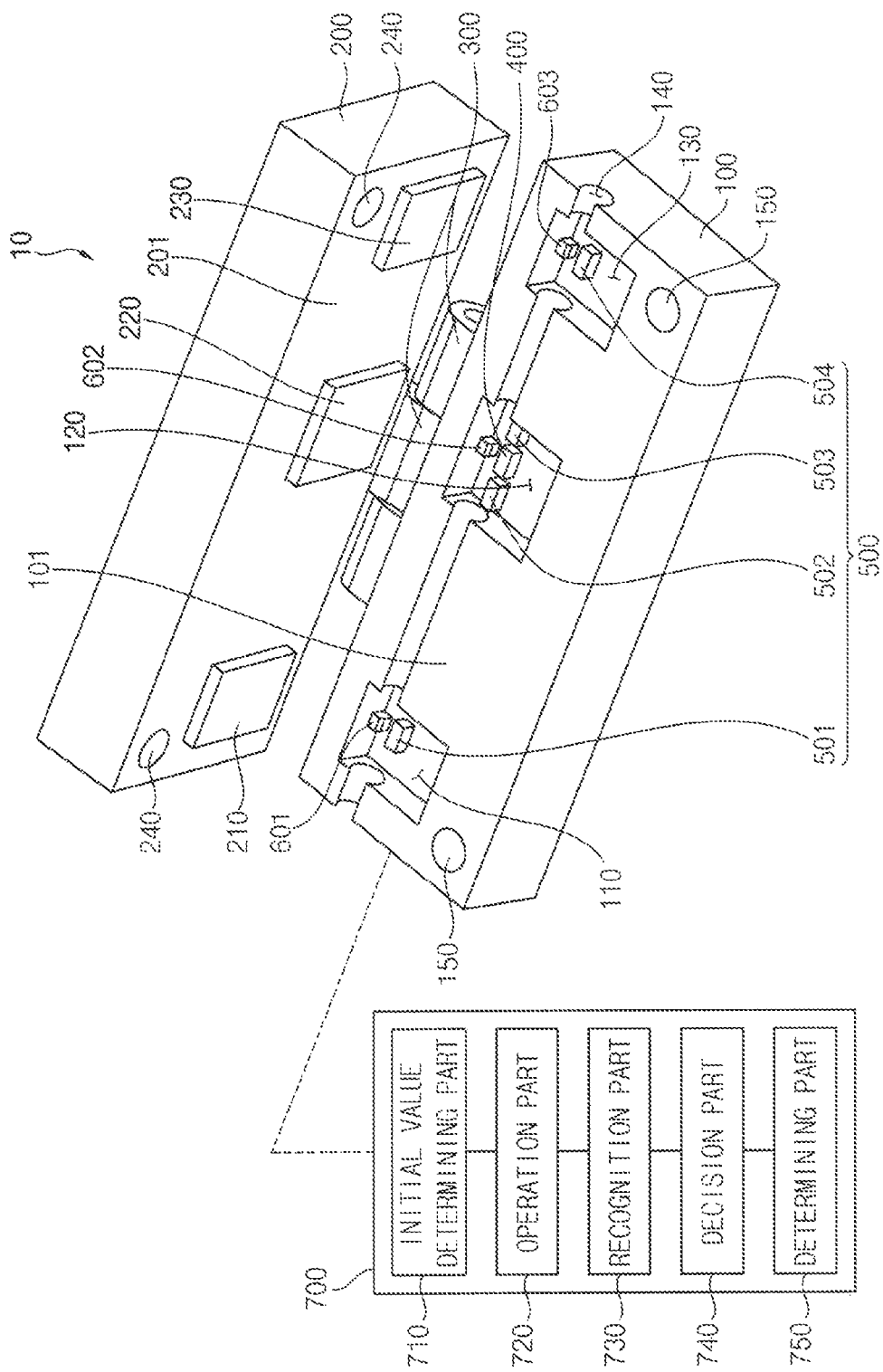
FIG. 1 is a perspective view illustrating a flow meter for an electric drug injection pump according to an example embodiment of the present invention.

| * Reverence numerals | |
|---|---|
| 10: flow meter | 100: lower case |
| 110, 120, 130: groove | 140: extending groove |
| 150: lower combination part | 200: upper case |
| 210, 220, 230: pressing part | 240: upper combination part |
| 300: connecting part | 400: heater |
| 500: temperature sensor part | 501, 502, 503, 504: temperature sensor |
| 601, 602, 603: supporting part | |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention is described more fully hereinafter with Reference to the accompanying drawings, in which embodiments of the invention are shown.

Figure 2:
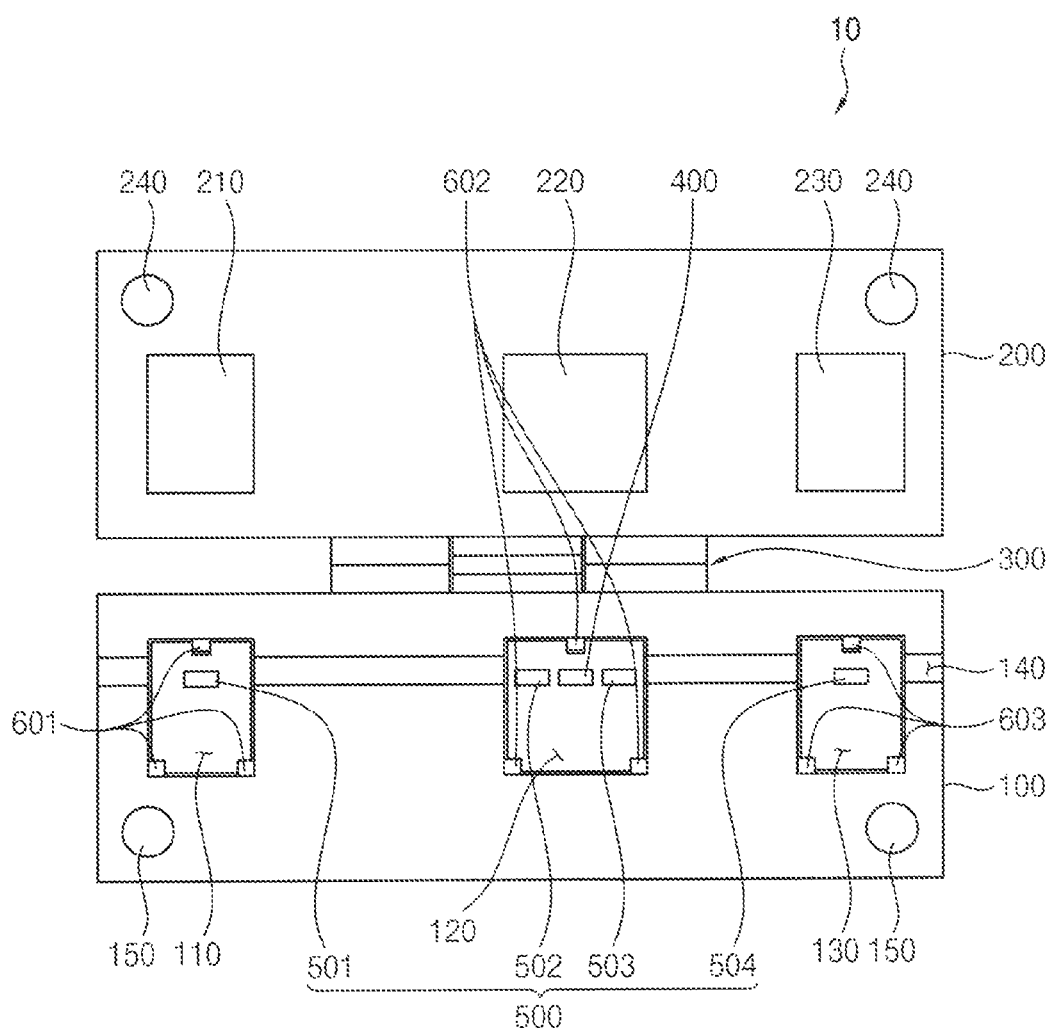
FIG. 2 is a plan view illustrating the flow meter of FIG. 1.
Figure 3:
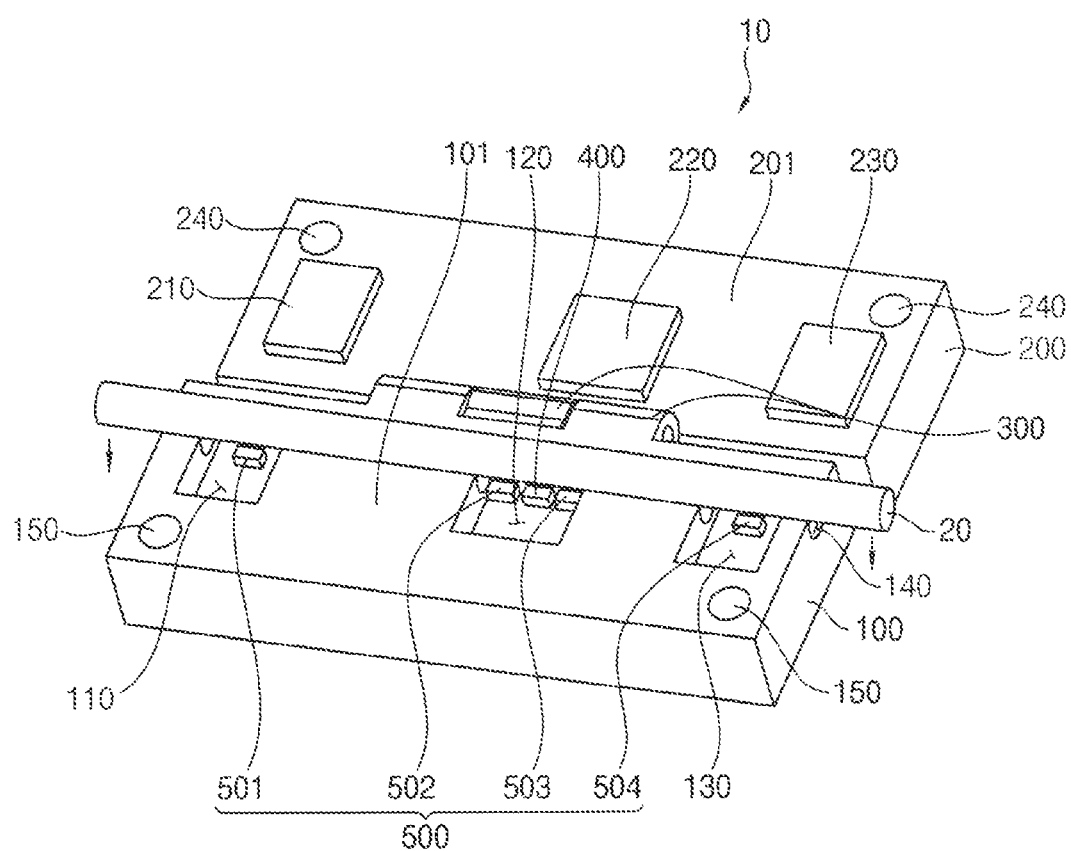
FIG. 3 is a perspective view illustrating a drug injection tube disposed in the flow meter of FIG. 1.

FIG. 1 is a perspective view illustrating a flow meter for an electric drug injection pump according to an example embodiment of the present invention. FIG. 2 is a plan view illustrating the flow meter of FIG. 1. FIG. 3 is a perspective view illustrating a drug injection tube disposed in the flow meter of FIG. 1.

Referring to FIG. 1, FIG. 2 and FIG. 3, the flow meter 10 according to the present example embodiment measures a flux or a flow of a fluid passing through a drug injection tube 20 of the electric drug injection pump. The drug normally passes through the drug injection tube 20 and thus the flow meter 10 measures the flux or the flow of the drug. Hereinafter, the flow means the flow rate or the flux, and the flow is used for the convenience of the explanation.

However, the flow meter 10 may be used for measuring the flow of various kinds of fluid passing through a specific tube, not limited to the drug.

Thus, although not shown in the figure, the flow meter 10 may be equipped to a drug injection pump or a drug injection device, and the flow meter 10 may be manufactured into a specific device so as to be selectively used for the drug injection pump or the drug injection device.

Here, the flow meter 10 includes a lower case 100, an upper case 200, a connecting part 300, a heater 400, a temperature sensor part 500, a supporting part and a control unit 700.

The lower case 100 may have a rectangular block shape as illustrated in the figure, but an outer shape of the lower case may be variously changed.

The upper case 200 may have the rectangular block shape, too, as illustrated in the figure, and an outer shape of the upper case 200 may match the outer shape of the lower case 100.

Here, the upper case 200 and the lower case 100 are connected with each other by the connecting part 300, with various kinds of connecting methods. In the present example embodiment, for example, the upper case 200 and the lower case 100 may be connected with each other with a rotational connecting method.

The connecting part 300 connects a first side of the lower case 100 with a first side of the upper case 200, and thus, the upper case 200 rotates with respect to the lower case 100 and a lower surface 201 of the upper case 200 makes contact with an upper surface 101 of the lower case 100.

Accordingly, the lower case 100 and the upper case 200 face each other, and the tube 20 is fixed between the lower case 100 and the upper case 200, and then the flow of the fluid passing through the tube 20 is measured with the tube 20 fixed.

A plurality of grooves is formed at the lower case 100, and the grooves, as illustrated in the figure, may be three, including first, second and third grooves 110, 120 and 130.

The first to third grooves 110, 120 and 130 are spaced apart from each other, and thus each of the grooves 110, 120 and 130 is separately disposed.

In addition, each of the first to third grooves 110, 120 and 130 is concaved from the upper surface 101 of the lower case 100, and thus a specific space is formed at each of the first to third grooves 110, 120 and 130.

Then, in the specific space of each of the first to third grooves 110, 120 and 130, the temperature sensor part 500, the heater 400 and the supporting part are disposed.

Here, each of the first to third grooves 110, 120 and 130 may have a rectangular shape in a plan view, but not limited thereto, and may have various kinds of shapes.

In addition, an extending groove 140 is formed at the lower case 100. The extending groove 140 extends in a straight line to connect or to cross the first to third grooves 110, 120 and 130. Like the first to third grooves 110, 120 and 130, the extending groove 140 is concaved from the upper surface 101 of the lower case 100.

The tube 20 is inserted into and fixed into the extending groove 140, and thus when a cross-section of the tube 20 has a circular shape, a cross-section of the extending groove 140 also has a rounded shape. Thus, the tube 20 is properly inserted into and fixed into the extending groove 140.

Here, considering the size of the cross-section of the tube 20, a curvature or a diameter of the rounded shape of the extending groove 140 may be designed. Normally, the tube 20 is flexible, and thus the size and the shape of the extending groove 140 should not to be the same as those of the tube 20. However, the size and the shape of the extending groove 140 may be formed such that the tube 20 may be properly fixed and inserted into the extending groove 140.

In the present example embodiment, the temperature of the fluid passing through the tube 20 should be measured with the fluid flowing straightly, to increase an accuracy of the measured result. Thus, the extending groove 140 extends straightly to pass by the first to third grooves 110, 120 and 130.

The heater 400 is disposed at a center of the second groove 120, and the heater 400 includes a heating device to generate a heat. The heat from the heater 400 heats the fluid passing through the tube 20.

Here, the heater 400 may be heating device generating the heat in itself, or may be heated using an electric or heat energy supplied from outside.

For example, the heater 400 may be a micro heater having a relatively smaller heat capacity. Alternatively, the heater 400 may be a heater having a relatively larger heat capacity.

When the heater 400 is the micro heater, the sensitivity of the measured results may be increased, compared to the heater having the larger heat capacity, so that the heat capacity of the heater 400 may be properly selected considering the fluid, the circumstances, the range of the temperatures, and so on.

In addition, as illustrated in FIG. 2, the heater 400 is aligned with an extending line of the extending groove 140, so that the heater 400 may make contact with a lower surface of the tube 20. Thus, the heat from the heater 400 is effectively transferred to the fluid through the tube 20, with minimizing the heat loss.

Accordingly, the fluid passing through the tube 20 is heated by the heat from the heater 400, and the temperature of the fluid is increased.

The temperature sensor part 500 includes a plurality of first to fourth temperature sensors 501, 502, 503 and 504, and each of the temperature sensors 501, 502, 503 and 503 measures the temperature of the fluid passing through the tube 20.

The first temperature sensor 501 is positioned at the first groove 110, the second and third temperature sensors 502 and 503 are positioned at the second groove 120, and the fourth temperature sensor 504 is positioned at the third groove 130.

Here, the first temperature sensor 501 is located at a center of the first groove 110, and the fourth temperature sensor 504 is located at a center of the third groove 130.

However, the heater 400 is located at the center of the second groove 120, and thus the second and third temperature sensors 502 and 503 are located at both sides of the heater 400 respectively.

In addition, like the heater 400, the first to fourth temperature sensors 501, 502, 503 and 504 are aligned along the extending line of the extending groove 140, and thus the first to fourth temperature sensors 501, 502, 503 and 504 make contact with the lower surface of the tube 20. Thus, the first to fourth temperature sensors 501, 502, 503 and 504 may measure the temperature of the fluid passing through the tube 20, more accurately and precisely.

As in FIG. 1, when the fluid passing through the tube 20 flows from the first groove 110 to the third groove 130, the first temperature sensor 501 measures an initial temperature of the fluid flowing into the tube 20.

Here, the temperature of the fluid measured by the first temperature sensor 501 may be defined as a reference temperature.

Alternatively, the fourth temperature sensor 504 measures the temperature of the fluid passing through and flowing out of the flow meter 10, and thus the fourth temperature sensor 504 measures the temperature of the fluid heated by the heater 400 and then flowing out of the tube 20.

The second temperature sensor 502 is disposed adjacent to the heater 400, and measures the temperature of the fluid before being heated by the heater 400. However, since the second temperature sensor 502 is disposed adjacent to the heater 400, the measured temperature in the second temperature sensor 502 may be higher than the measured temperature in the first temperature sensor 501.

Even though the measured temperature in the second temperature sensor 502 is higher than the measured temperature in the first temperature sensor 501, the heating effect is decreased as an amount of the flow of the fluid passing through the tube 20 increases, and thus the measured temperature in the second temperature sensor 502 may be decreased as the amount of the flow of the fluid increases.

Accordingly, the temperature measured in the second temperature sensor 502 is gradually decreased as the amount of the flow of the fluid flowing into the tube 20 is gradually increased.

The third temperature sensor 503 is disposed adjacent to the heater 400, and the third temperature sensor 503 measures the temperature of the fluid after being heated by the heater 400.

Here, the temperature of the fluid is increased as the fluid is heated by the heater 400. However, as explained above, as the amount of the flow of the fluid increases, even though the fluid is heated by the heater 400, the temperature of the fluid may be increased, decreased or maintained constantly according to the heat supplied to the fluid.

Thus, the temperature of the fluid measured by the third temperature sensor 503 may be variously and complicatedly changed according to the heating effect of the heater 400 and the increasing state of the flow of the fluid.

Accordingly, the measured value in the first temperature sensor 501 may be defined as the reference temperature. The measured value in the second temperature sensor 502 may mean an amount of the decrease of the temperature of the heater 400 according to the increase of the flow of the fluid. The measured value in the third temperature sensor 503 may mean an amount of the decrease of the temperature of the heater 400 according to the passing of the fluid, and may mean an increasing effect of the temperature of the fluid heated in the heater 400. The measured value in the fourth temperature sensor 504 may mean an increasing effect of the fluid.

A relationship between the measured value in the first to fourth temperature sensors 501, 502, 503 and 504 and the flow of the fluid, will be explained below referring to FIG. 5.

As explained above, the upper case 200 is combined with the lower case 100, and a plurality of first to third pressing parts 210, 220 and 230 is protruded from the lower surface 201 of the upper case 200.

Here, the first pressing part 210 is aligned with the first groove 110, the second pressing part 220 is aligned with the second groove 120, and the third pressing part 230 is aligned with the third groove 130.

In addition, each of the first to third pressing parts 210, 220 and 230 is protruded with a predetermined thickness, and the thickness of each of the first to third pressing parts 210, 220 and 230 is smaller than a depth of each of the first to third grooves 110, 120 and 130.

Here, the shape of each of the first to third pressing parts 210, 220 and 230 is substantially same as the shape of the each of the first to third grooves 110, 120 and 130, in a plan view. However, the size of each of the first to third pressing parts 210, 220 and 230 is smaller than that of each of the first to third grooves 110, 120 and 130, so that each of the first to third pressing parts 210, 220 and 230 is inserted into each of the first to third grooves 110, 120 and 130.

When the upper case 200 is combined with the lower case 100, each of the first to third pressing parts 210, 220 and 230 is inserted into each of the first to third grooves 110, 120 and 130.

Accordingly, as each of the first to third pressing parts 210, 220 and 230 is inserted into each of the first to third grooves 110, 120 and 130, when the tube 20 is positioned at the extending groove 140 crossing the first to third grooves 110, 120 and 130, the tube 20 is pressed by the first to third pressing parts 210, 220 and 230.

In addition, as the tube 20 is pressed downwardly by the first to third pressing parts 210, 220 and 230, the lower surface of the tube 20 naturally makes contact with the first to fourth temperature sensors 501, 502, 503 and 504 and the heater 400.

The contact state mentioned above will be explained below referring to FIG. 4A and FIG. 4B.

A lower combination part 150 is formed at both sides of the lower case 100, and an upper combination part 240 corresponding to the lower combination part 150 is formed at both sides of the upper case 200.

Thus, when the lower case 100 is combined with the upper case 200, the lower combination part 150 is combined with the upper combination part 240.

Here, each of the lower and upper combination parts 150 and 240 may be a permanent magnet.

The supporting part is formed at the first to third grooves 110, 120 and 130, and a plurality of supporting parts may be formed at each of the first to third grooves 110, 120 and 130, as illustrated in FIG. 2.

For example, a first supporting part 601 may include three supporting parts, one of which is disposed at a first side of the first groove 110 and two of which are disposed at a second side of the first groove 110. Likewise, a second supporting part 602 may include three supporting parts, one of which is disposed at a first side of the second groove 120 and two of which are disposed at a second side of the second groove 120. Further, a third supporting part 603 may include three supporting parts, one of which is disposed at a first side of the third groove 130 and two of which are disposed at a second side of the third groove 130.

Each of the first to third supporting parts 601, 602 and 603 has a height substantially same as a height of each of the temperature sensors 501, 502, 503 and 504 and a height of the heater 400. Thus, the first to third supporting parts 601, 602 and 603 respectively supports the first to third pressing parts 210, 220 and 230 inserted into the first to third grooves 110, 120 and 130.

Each of the first to third supporting parts 601, 602 and 603 makes contact with each of the first to third pressing parts 210, 220 and 230, to prevent the first to third pressing parts 210, 220 and 230 from being inserted over a predetermined depth.

The tube 20 is prevented from being excessively pressed by the first to third pressing parts 210, 220 and 230, and thus, the fluid passing through the tube 20 is prevented from being interrupted by the pressed tube and the tube 20 is prevented from being damaged.

The control unit 700 controls an operation of the flow meter 10, and includes an initial value determining part 710, and an operation part 720, a recognition part 730, a decision part 740 and a determining part 750.

The initial value determining part 710 determines an initial value of the flow of the fluid passing through the temperature sensor part 500 and the tube 20, and the operation part 720 supplies the fluid to the tube 20.

In addition, the recognition part 730 recognizes the flow direction of the fluid passing through the tube 20, based on the temperature measured in the temperature sensor part 500. The decision part 740 decides an applied equation for measuring the flow of the fluid, based on the temperature measured in the temperature sensor part 500.

The determining part 750 determines the flow of the fluid, based on the decided equation.

A specific control of the control unit 700 will be explained below in a method for measuring the flow of the fluid.

Figure 4A:
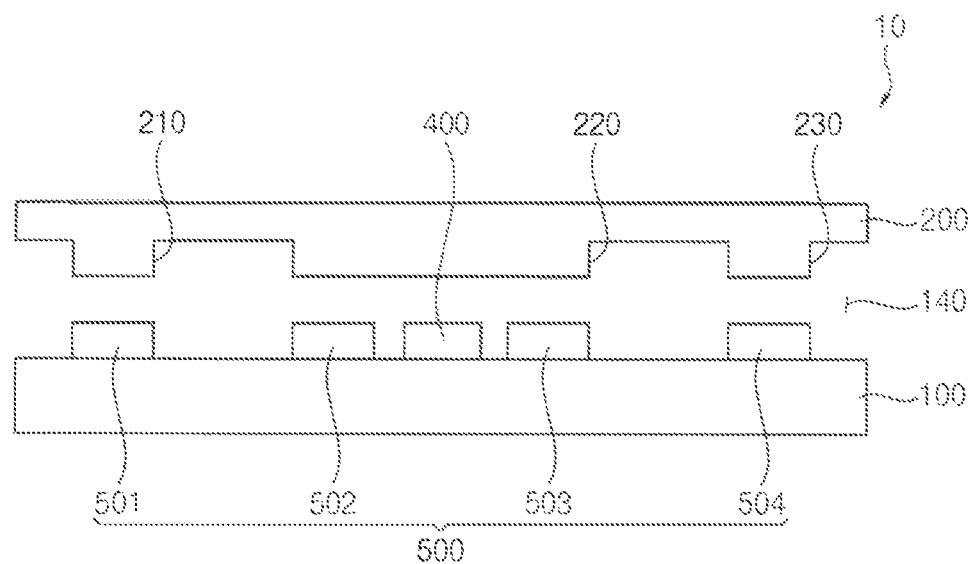
FIG. 4A is a cross-sectional view along an extending groove in the flow meter of FIG. 1.
Figure 4B:
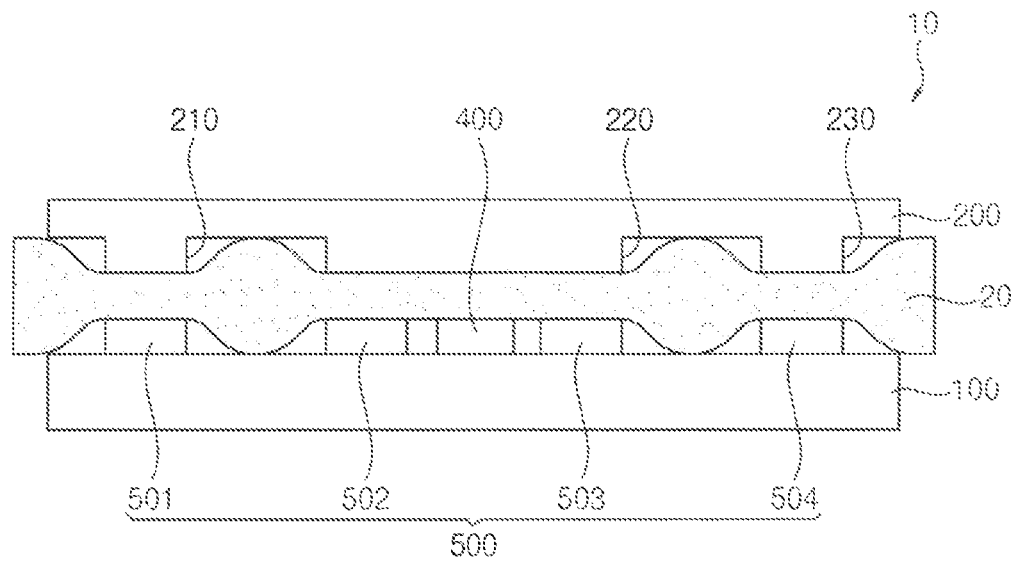
FIG. 4B is a cross-sectional view along the extending groove in the flow meter with the drug injection tube of FIG. 3.

FIG. 4A is a cross-sectional view along an extending groove in the flow meter of FIG. 1, and FIG. 4B is a cross-sectional view along the extending groove in the flow meter with the drug injection tube of FIG. 3.

Referring to FIG. 4A, as explained above, with the upper case 200 combined with the lower case 100, the first temperature sensor 501 and the first pressing part 210 disposed over the first temperature sensor 501 are aligned in the extending groove 140.

In addition, the second pressing part 220 is aligned over with the second temperature sensor 502, the heater 400 and the third temperature sensor 503. The third pressing part 230 is aligned over with the fourth temperature sensor 504.

Then, referring to FIG. 4B, when the tube 20 is disposed in the extending groove 140, the tube 20 is downwardly pressed by the first to third pressing parts 210, 220 and 230. Thus, the lower surface of the tube 20 makes direct contact with the first temperature sensor 501, the second temperature sensor 502, the heater 400, the third temperature sensor 503 and the fourth temperature sensor 504.

Thus, the fluid passing through the tube 20 may be heated by the heater 400 more effectively, and likewise, the temperature of the fluid passing through the tube 20 may be measured by the first to fourth temperature sensors 501, 502, 503 and 504 more accurately and precisely.

In the present example embodiment, the temperature sensor part and the heater do not make direct contact with the fluid inside of the tube 20 for the measuring and the heating, and thus the heating effect or the accuracy of the measurement may be decreased. Thus, as explained above, the temperature sensor part and the heater make direct contact with the tube 20, to increase the heating effect and the measuring accuracy.

In addition, since the temperature sensor part and the heater do not make direct contact with the fluid, the drug may be prevented from being polluted and the temperature sensor part and the heater may be reuse repeatedly. Thus, the usability and the durability may be more increased.

Hereinafter, the method for measuring the flow of the fluid using the flow meter 10 is explained in detail.

Figure 5:
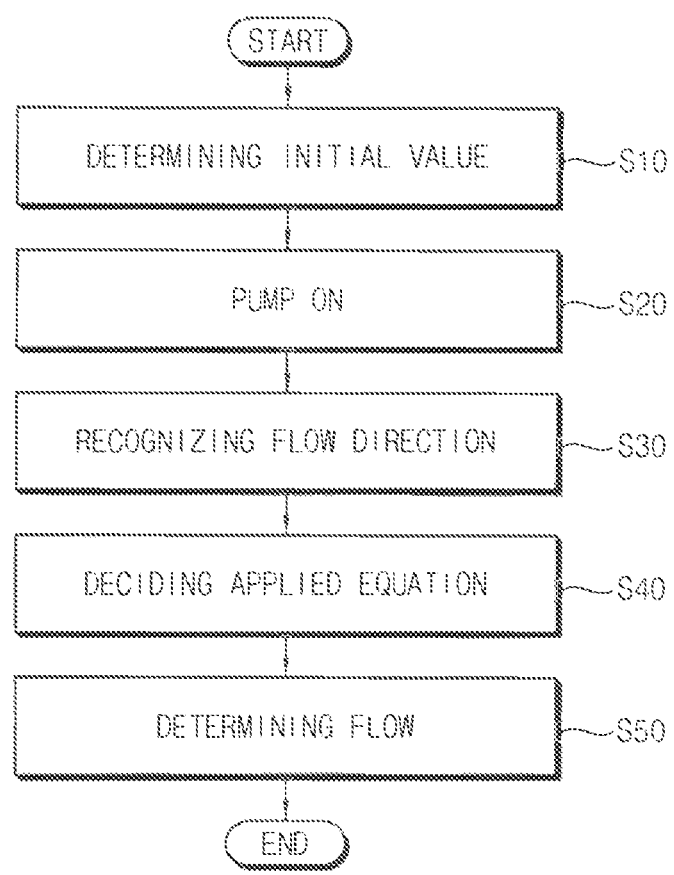
FIG. 5 is a flow chart illustrating a method for measuring a flow rate using the flow meter of FIG. 1.
Figure 6:
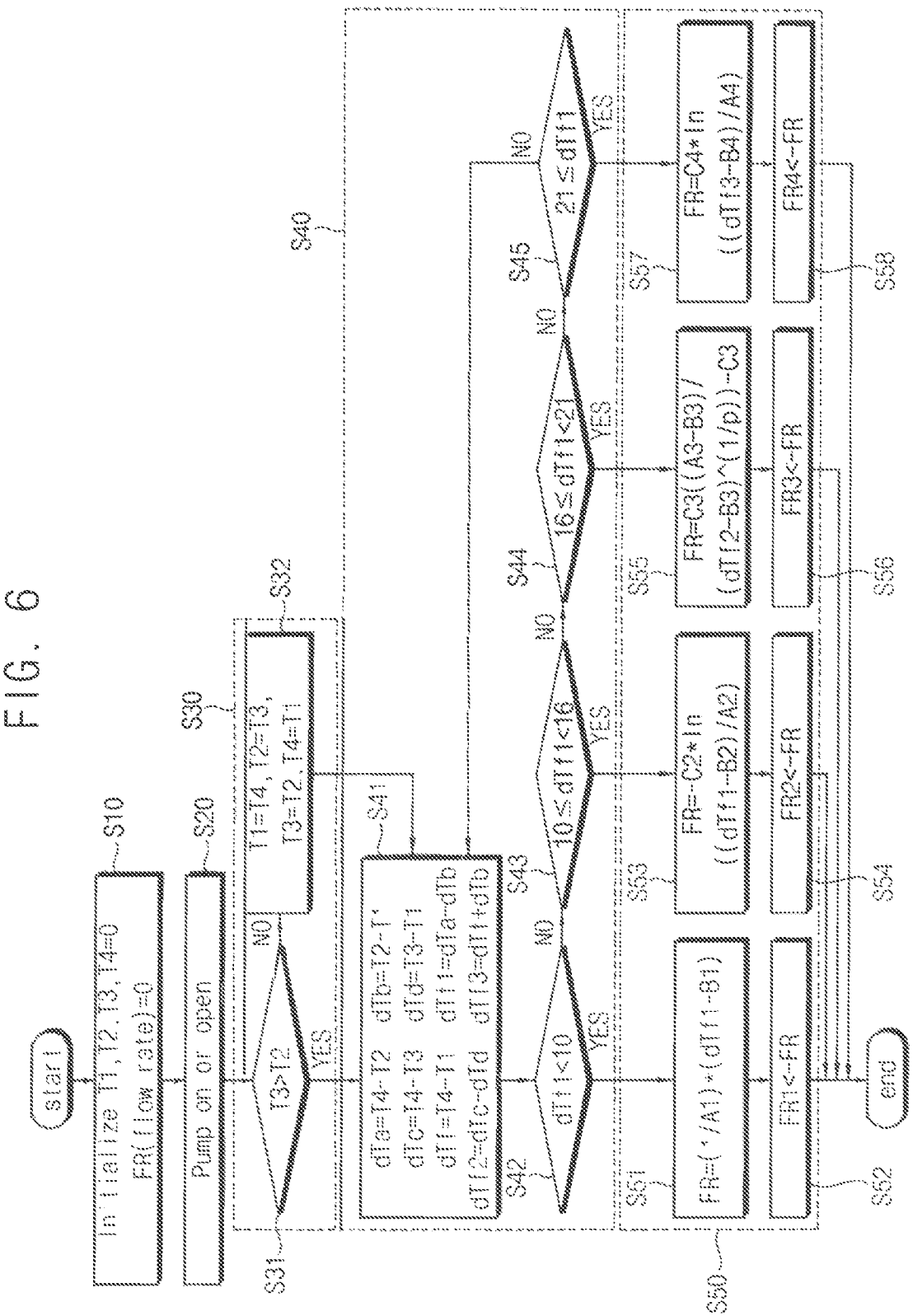
FIG. 6 is a flow chart illustrating the method for measuring the flow rate of FIG. 5, more specifically.

FIG. 5 is a flow chart illustrating a method for measuring a flow rate using the flow meter of FIG. 1. FIG. 6 is a flow chart illustrating the method for measuring the flow rate of FIG. 5, more specifically.

Referring to FIG. 5 and FIG. 6, in the method for measuring the flow using the flow meter 10, first, the initial value is determined by the initial value determining part 710 (step S10).

Here, as for the initial value, an initial value of the flow of the fluid (FR, flow rate) passing through the tube 20 is determined to be 0 (zero), and initial values of each of the first to fourth temperatures (T1~T4) in the first to fourth temperature sensors 501, 502, 503 and 504 are determined to be 0 (zero).

Then, via the operation part 720, the fluid starts to flow into the tube 20 (step S20).

Here, the operation part 720 may operate the pump driving the flow of the fluid, or may open a valve of the tube, to induce the flow of the fluid.

Then, in the recognition part 730, the direction of the flow of the fluid passing through the tube 20 is recognized based on the temperature measured in the temperature sensor part 500 (step S30).

For example, whether the third temperature T3 measured in the third temperature sensor 503 is higher than the second temperature T2 measured in the second temperature sensor 502 is decided (step S31). Then, when the third temperature T3 is higher than the second temperature T2, the fluid is decided to flow from the first temperature sensor 501 to the fourth temperature sensor 504.

Here, when the third temperature T3 is lower than the second temperature T2, the fluid is decided to flow from the fourth temperature sensor 504 to the first temperature sensor 501. In addition, in the equation for measuring the flow mentioned below, the first temperature T1 measured in the first temperature sensor 501 is regarded to the fourth temperature T4. Likewise, the second temperature T2 is regarded to the third temperature T3, the third temperature T3 is regarded to the second temperature T2, and the fourth temperature T4 is regarded to the first temperature T1.

Accordingly, since the fluid is heated in the heater 400, the temperature measured in the temperature sensor at a rear side of the heater 400 along the flow direction is higher than the temperature measured in the temperature sensor at a front side of the heater 400 along the flow direction. Based on the above, the recognition part 730 recognizes the flow direction.

Then, the decision part 740 decides an applied equation for measuring the flow of the fluid based on the temperature measured in the temperature sensor part 500 (step S40).

For example, first, based on the temperatures T1, T2, T3 and T4 measured in the first to fourth temperature sensors 501, 502, 503 and 504, first to fifth temperature differences dTa, dTb, dTc, dTd and dTf are calculated, and first to third comparison values dTf1, dTf2 and dTf3 are calculated (step S41).

Here, the first temperature difference dTa is a difference between the fourth temperature T4 and the second temperature T2, the second temperature difference dTb is a difference between the second temperature T2 and the first temperature T1, the third temperature difference dTc is a difference between the fourth temperature T4 and the third temperature T3, the fourth temperature difference dTd is a difference between the third temperature T3 and the first temperature T1, and the fifth temperature difference dTf is a difference between the fourth temperature T4 and the first temperature T1, In addition, the first comparison value dTf1 is a difference between the first temperature difference dTa and the second temperature difference dTb (dTa−dTb), the second comparison value dTf2 is a difference between the third temperature difference dTc and the fourth temperature difference dTd (dTc−dTd), and the third comparison value dTf3 is a sum of the fifth temperature difference dTf and the second temperature difference dTb.

Then, the applied equation is decided based on the first comparison value dTf1.

For example, whether the first comparison value dTf1 is less than 10° C. is decided (step S42), whether the first comparison value dTf1 is between 10° C. and 16° C. is decided (step S43), whether the first comparison value dTf1 is between 16° C. and 21° C. is decided (step S44), and whether the first comparison value dTf1 is more than 21° C. is decided (step S45), and then the applied equation used in determining the flow (step S50) explained below may be differently selected.

Accordingly, based on the first comparison value dTf1, the equation in determining the flow is differently selected, so that the flow of the fluid passing through the tube 20 may be measured more accurately and precisely. In addition, the flow may be measured more sensitively.

Then, in the determining part 750, based on the selected equation in the decision part 740, the flow of the fluid passing through the tube 20 is determined (step S50).

For example, when the first comparison value dTf1 is less than 10° C., in the determining part 750, the below equation (1) is used to determine the flow of the fluid (FR1) passing through the tube 20 (step S51 and step S52).

$$FR( = FR1) = \frac{1}{A1}(dTf1 - B1) \qquad \text{Equation (1)}$$

Figure 8A:
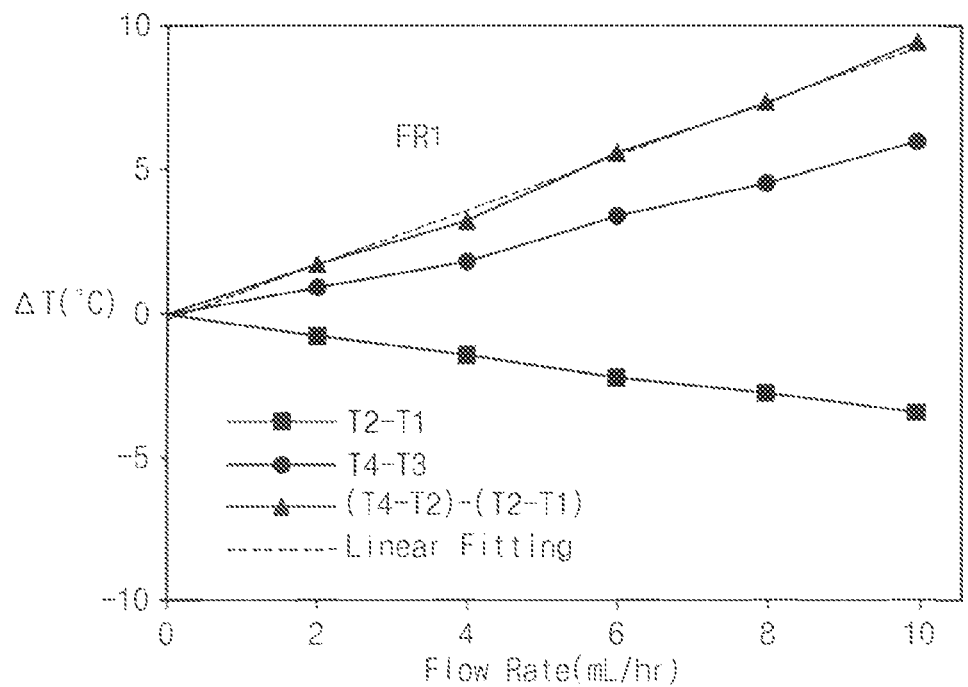
FIG. 8A, FIG. 8B and FIG. 8C are graphs showing a temperature and a flow rate obtained from the method for measuring the flow rate of FIG. 5.

(Here, A1 and B1 are constants, and in FIG. 8A, for example, A1=0.106 and B1=0.197)

Alternatively, when the first comparison value dTf1 is between 10° C. and 16° C., in the determining part 750, the below equation (2) is used to determine the flow of the fluid (FR2) passing through the tube 20 (step S53 and step S54).

$$FR( = FR2) = -C2\ln\left(\frac{dTf1 - B2}{A2}\right) \qquad \text{Equation (2)}$$

Figure 8B:
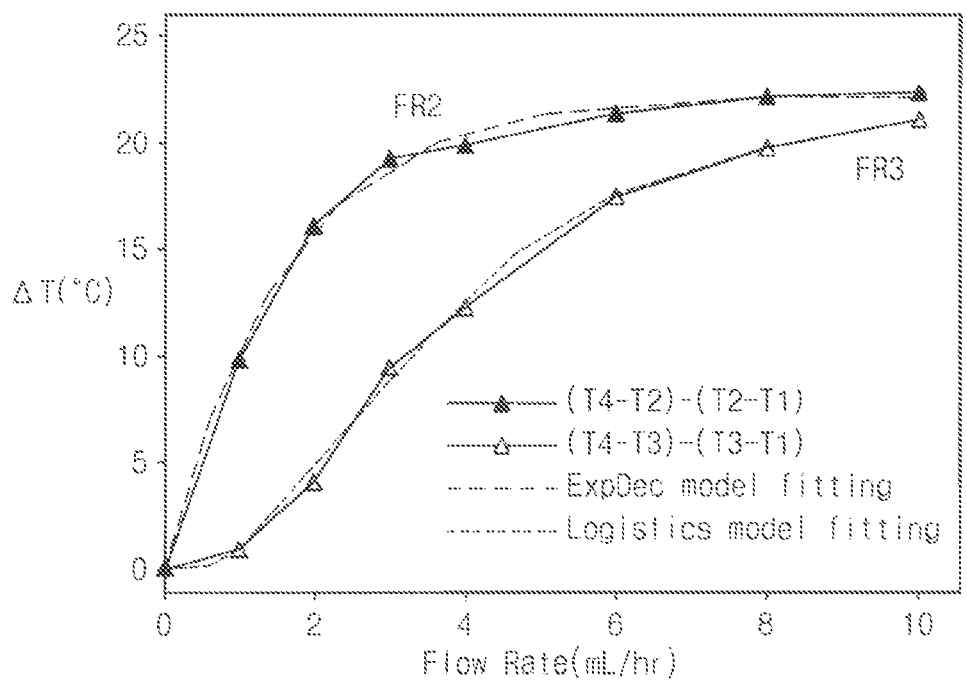

(Here, A2, B2 and C2 are constants, and in FIG. 8B, for example, A2=−22.36, B2=22.26 and C2=1.6)

In addition, when the first comparison value dTf1 is between 16° C. and 21° C., in the determining part 750, the below equation (3) is used to determine the flow of the fluid (FR3) passing through the tube 20 (step S55 and step S56).

$$FR( = FR3) = C3\left(\frac{A3 - B3}{(dTf2 - B3)^{\frac{1}{p}}}\right) - C3 \qquad \text{Equation (3)}$$

(Here, A3, B3, C3 and p are constants, and in FIG. 8B, for example, A3=−0.08, B3=23.04, C3=3.64 and p=2.38)

Further, when the first comparison value dTf1 is over 21° C., in the determining part 750, the below equation (4) is used to determine the flow of the fluid (FR4) passing through the tube 20 (step S57 and step S58).

$$FR(=FR4)=C4*\ln((dTf3-B4)/A4) \qquad \text{Equation (4)}$$

Figure 8C:
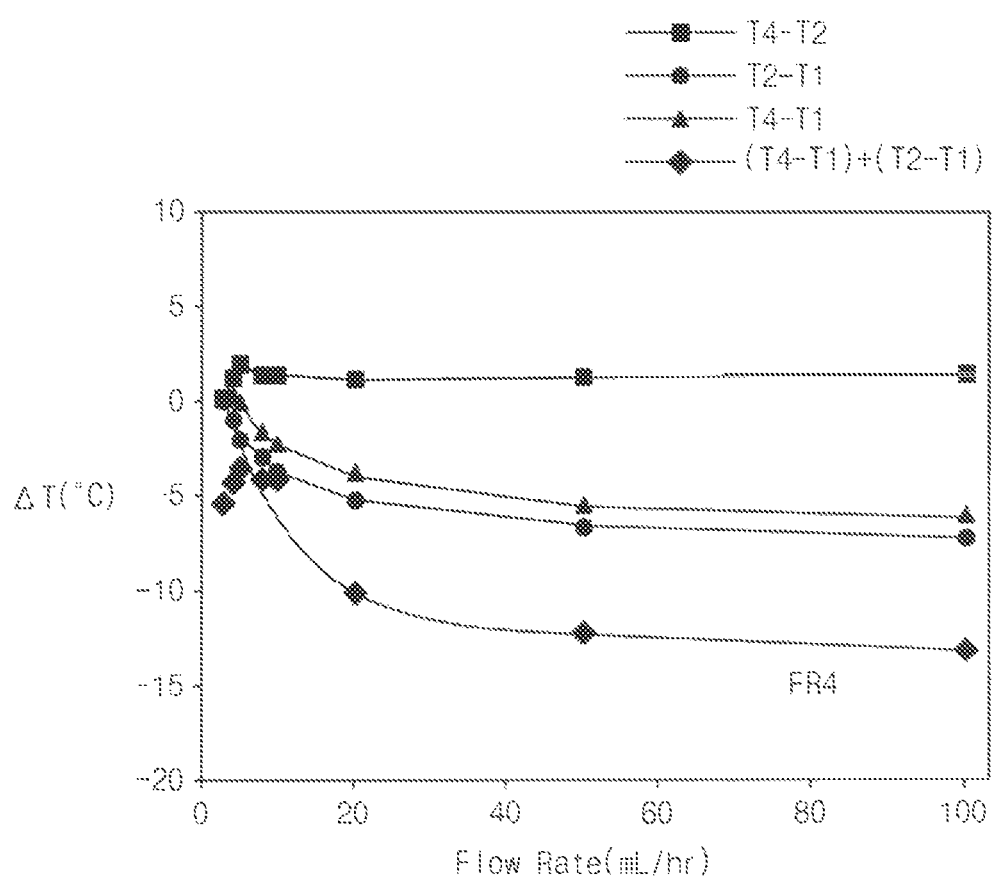

(Here, A4, B4 and C4 are constants, and in FIG. 8C, for example, A4=16.8, B4=15.6 and C4=−10.7)

Accordingly, in the determining part 750, based on the range of the first comparison value dTf1, the applied equation for calculating the flow of the fluid is variously selected. Thus, based on the selected equation, the flow of the fluid passing through the tube 20 may be properly calculated using the temperature measured in the temperature sensor part 500.

Figure 7:
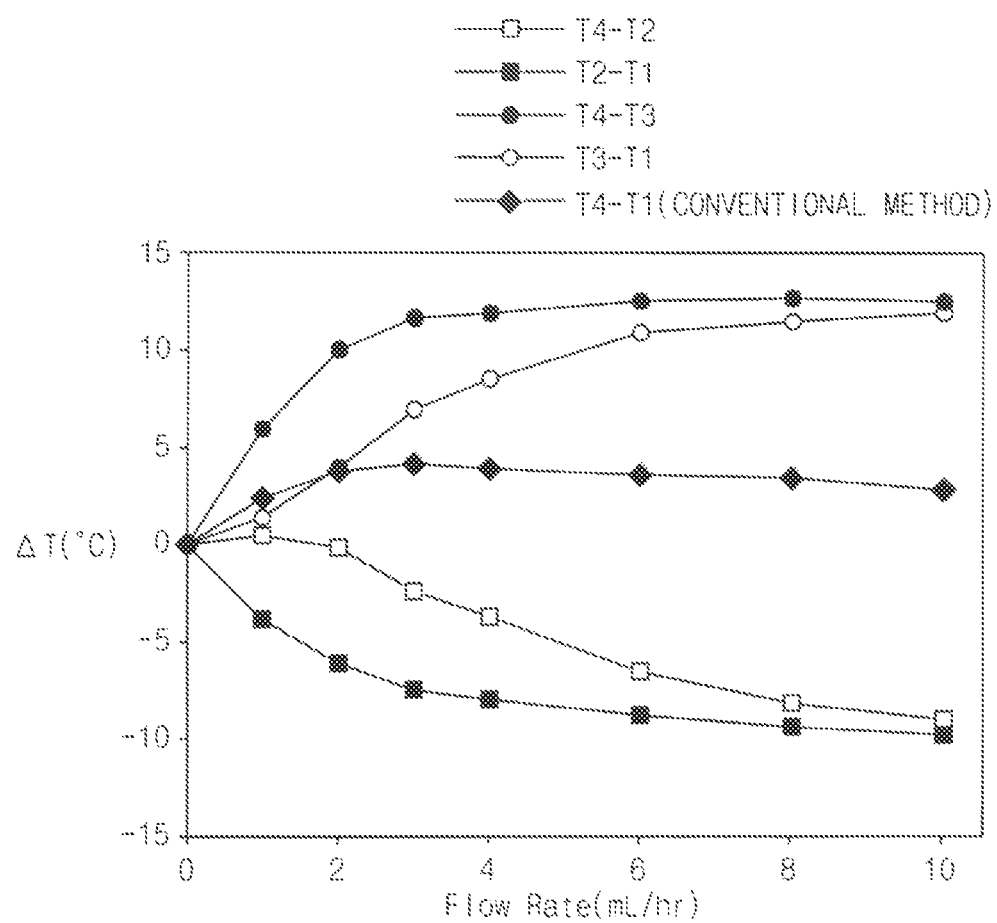
FIG. 7 is a graph showing a temperature and a flow rate obtained from the conventional heat-based flow meter.

FIG. 7 is a graph showing a temperature and a flow rate obtained from the conventional heat-based flow meter.

Referring to FIG. 7, in the conventional heat-based flow meter, the first and fourth temperature sensors 501 and 504 are merely equipped, and thus the first temperature T1 measured in the first temperature sensor 501 and the fourth temperature T4 measured in the fourth temperature sensor 504 are only obtained.

Thus, as illustrated in FIG. 7, only T4−T1 which is a temperature difference may be obtained, and the relationship between the temperature difference T4−T1 and the flow of the fluid may be merely obtained.

However, referring to the relationship between T4−T1 and the flow of the fluid in FIG. 7, the change or the variation of the temperature difference T4−T1 according to the flow of the fluid is very small, and thus the flow of the fluid is hard to be obtained based on the temperature difference T4−T1.

Alternatively, in FIG. 7, based on the temperatures T1~T4 measured in the four temperature sensors, various information like the first temperature difference dTa (T4−T2), the second temperature difference dTb (T2−T1), the third temperature difference dTc (T4−T3), the fourth temperature difference dTd (T3−T1) and the fifth temperature difference dTf (T4−T1) may be obtained. As illustrated in the figure, each temperature difference may be changed relatively largely according to the flow of the fluid.

Accordingly, the information on the flow of the fluid may be obtained from the first to fifth temperature differences more accurately and more precisely.

However, in the present example embodiment, the relationships among the first to fifth temperature differences are defined as the equations mentioned above, and thus as illustrated in FIG. 8A, FIG. 8B and FIG. 8C, the relationship between the temperature and the flow of the fluid may be defined as a single function. Then, based on the single function, the flow of the fluid may be measured more accurately, precisely and sensitively based on the fourth measured temperatures.

FIG. 8A, FIG. 8B and FIG. 8C are graphs showing a temperature and a flow rate obtained from the method for measuring the flow rate of FIG. 5.

FIG. 8A and FIG. 8B are the graphs showing the relationship between the actually measured temperature and the obtained flow of the fluid, via using the method for measuring the flow explained referring to FIG. 5 and FIG. 6.

For example, when the first comparison value dTf1 is less than 10° C., the flow (FR1), as illustrated in FIG. 8A, is defined as a first-order function like the equation (1) in the relationship with the first comparison value dTf1, and thus the flow (FR1) may be obtained using the equation (1) precisely and accurately.

Here, the constant in the first-order function in FIG. 8A, is already explained in the equation (1).

Alternatively, when the first comparison value dTf1 is between 10° C. and 16° C., the flow (FR2), as illustrated in FIG. 8B, is defined as a logarithmic function like the equation (2) in the relationship with the first comparison value dTf1, and thus the flow (FR2) may be obtained using the equation (2) precisely and accurately.

Here, the constant in the logarithmic function in FIG. 8B, is already explained in the equation (2).

In addition, when the first comparison value dTf1 is between 16° C. and 21° C., the flow (FR3), as illustrated in FIG. 8B, is defined as an exponential function like the equation (3) in the relationship with the second comparison value dTf2, and thus the flow (FR3) may be obtained using the equation (3) precisely and accurately.

Here, the constant in the exponential function in FIG. 8B, is already explained in the equation (3).

Further, when the first comparison value dTf1 is over 21° C., the flow (FR4), as illustrated in FIG. 8C, is defined as a logarithmic function like the equation (4) in the relationship with the third comparison value dTf3, and thus the flow (FR3) may be obtained using the equation (4) precisely and accurately.

Here, the constant in the logarithmic function in FIG. 8C, is already explained in the equation (4).

As illustrated in FIG. 8C, the equation (4) which is defined in case that the first comparison value dTf1 is over 21° C. may obtain the flow of the fluid more effectively when the flow of the fluid is relatively larger (for example, 10~100 mL/hr).

Accordingly, in the present example embodiment, when the flow of the fluid is relatively smaller (for example, 0~10 mL/hr), the flow of the fluid may be obtained using the equations (1) to (3). In addition, when the flow of the fluid is relatively larger (for example, 10~100 mL/hr), the flow of the fluid may be obtained using the equation (4).

Thus, for the range of the flow of the fluid between 0 mL/hr and 100 mL/hr, the temperature and the flow of the fluid may be effectively obtained.

Accordingly, in the present example embodiment, based on the first to fourth temperatures measured in the first to fourth temperature sensors, the first to fifth temperature differences, and the first to third comparison values are defined. Then, based on the first comparison value, the equations for calculating the flow different from each other are obtained, so that the temperature and the flow of the fluid may be effectively, accurately, precisely and sensitively obtained in range of the flow of the fluid between 0 mL/hr and 100 mL/hr, compared to the conventional heat-based flow meter.

According to the example embodiments, in the conventional heat-based flow rate measuring device, the sensor makes direct contact with the fluid. However, in the present example embodiments, the temperature sensor part and the heater are disposed on an outer surface of the tube through which the fluid passes, so that the sensor does not make direct contact with the fluid and the flow rate may be precisely and accurately measured.

Here, the tube may be a fixed type or may be inserted or detached from the extending groove, so that the flow rate of the fluid passing through various kinds of tubes may be selectively measured if necessary. Thus, user's usability and convenience may be more increased.

Since the temperature sensor part and the heater are disposed on the outer surface of the tube, a pressing part is additionally equipped to press the tube to the temperature sensor part and the heater. Thus, the heating effect to the fluid and the measuring accuracy may be more increased.

Here, the temperature sensor part includes four temperature sensors, and the sensors are separately disposed at the plurality of grooves spaced apart from each other. Thus, the sensing information from each sensor may be separated and the temperature may be measured more accurately and more precisely.

For example, the second temperature sensor and the third temperature sensor are disposed at both sides of the heater, and separately measure the decreasing temperature of the heater when the fluid passes through, or the temperature of the fluid heated in the heater. Thus, the changes of the temperatures at various kinds of drug injection circumstances may be precisely and accurately detected, with the first temperature sensor measuring the reference temperature and the fourth temperature sensor measuring the temperature increasing. Further, when the flow rate is relatively lower, the above measuring may be more effective.

The above technology may be confirmed using an actual flow rate measuring method, and based on the difference of the temperatures measured by four temperature sensors, the relationship between the flow rate and the temperature may be obtained merely by using a proportional relationship or a log function relationship (or exponential function relationship). Thus, the flow rate may be detected more accurately and precisely.

For both of a range of relatively lower flow rate and a range of relatively higher flow rate, for example in the range of the flow rate between 0 mL/hr and 100 mL/hr, the precise and accurate flow rate may be detected or measured.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A flow meter comprising:
a lower case in which a plurality of grooves and an extending groove are formed, wherein the grooves are spaced apart from each other, wherein the extending groove extends along the grooves and a tube is positioned in the extending groove;
an upper case facing the lower case and combined with the lower case, to fix the tube;
a heater positioned at one of the grooves, to supply a heat to a fluid passing through the tube;
a temperature sensor part positioned at each of the grooves, to measure the temperature of the fluid passing through the tube; and
a control unit configured to decide an applied equation for measuring a flow of the fluid, based on the temperature measured in the temperature sensor part,
wherein the tube is positioned to make contact with the heater and the temperature sensor part,
wherein the grooves comprise first, second and third grooves which are sequentially disposed along a direction of a fluid passing through the tube,
wherein a first temperature sensor is disposed at the first groove, second and third temperature sensors and the heater are disposed at the second groove, and a fourth temperature sensor is disposed at the third groove,
wherein the first temperature sensor measures an initial temperature of the fluid flowing into the tube,
wherein the second and third temperature sensors measures a temperature of the fluid as a result of heating of the heater,
wherein the fourth temperature sensor measures a temperature of the fluid flowing out of the tube,
wherein in the deciding the applied equation, the applied equation is decided based on a range of a first comparison value which is a difference between a first temperature difference and a second temperature difference,
wherein the first temperature difference is a difference between the temperature measured by the fourth temperature sensor and the temperature measured by the second temperature sensor, and
wherein the second temperature difference is a difference between the temperature measured by the second temperature sensor and the temperature measured by the first temperature sensor.

2. The flow meter of claim 1, wherein the upper case comprises a plurality of pressing parts respectively arranged with the grooves, and the pressing parts press the tube to be tightly attached to the heater and the temperature sensor part.

3. The flow meter of claim 2, further comprising:
a plurality of supporting parts disposed at the grooves respectively, to support the pressing parts respectively.

4. The flow meter of claim 1, wherein the heater is disposed between the second temperature sensor and the third temperature sensor.

5. The flow meter of claim 1, wherein the second temperature sensor measures decrease of the temperature of the heater as the fluid passes through the heater, and the third temperature sensor measures one of decrease of the temperature of the heater as the fluid passes through the heater and measures the temperature of the fluid heated by the heater.

6. A method for measuring flow, comprising:
determining an initial value of flow of a fluid passing through a temperature sensor part and a tube;
supplying the fluid to the tube;
recognizing a flow direction of the fluid passing through the tube, based on a temperature measured by the temperature sensor part;
deciding an applied equation for measuring the flow of the fluid, based on the temperature measured by the temperature sensor part; and
determining the flow based on the applied equation,
wherein the temperature sensor part is located in a plurality of grooves and the plurality of grooves comprises first, second and third grooves which are sequentially disposed along a direction of a fluid passing through the tube,
wherein a first temperature sensor is disposed at the first groove, second and third temperature sensors and the heater are disposed at the second groove, and a fourth temperature sensor is disposed at the third groove,
wherein the first temperature sensor measures an initial temperature of the fluid flowing into the tube,
wherein the second and third temperature sensors measure a temperature of the fluid as a result of heating of the heater,
wherein the fourth temperature sensor measures a temperature of the fluid flowing out of the tube,
wherein in the deciding the applied equation, the applied equation is decided based on a range of a first comparison value which is a difference between a first temperature difference and a second temperature difference,
wherein the first temperature difference is a difference between the temperature measured by the fourth temperature sensor and the temperature measured by the second temperature sensor, and
wherein the second temperature difference is a difference between the temperature measured by the second temperature sensor and the temperature measured by the first temperature sensor.

7. The method of claim 6, wherein in the recognizing the flow direction of the fluid, the flow direction of the fluid is recognized by the temperature measured by the second and third temperature sensors respectively disposed at both sides of the heater.

8. The method of claim 6, wherein in the determining the flow, the flow is proportional to the first comparison value when the first comparison value is less than 10° C., and the flow has a logarithmic relationship with the first comparison value when the first comparison value is between 10° C. and 16° C.

9. The method of claim 6, wherein in the determining the flow, the flow has an exponential relationship with a second comparison value when the first comparison value is between 16° C. and 21° C.,
- wherein the second comparison is a difference between a third temperature difference and a fourth temperature difference,
- wherein the third temperature difference is a difference between the temperature measured by the fourth temperature sensor and the temperature measured by the third temperature sensor, and
- wherein the fourth temperature difference is a difference between the temperature measured by the third temperature sensor and the temperature measured by the first temperature sensor.

10. The method of claim 6, wherein in the determining the flow, the flow has a logarithmic relationship with a third comparison value when the first comparison value is over 21° C.,
- wherein the third comparison value is the sum of a fifth temperature difference and the second temperature difference, and
- wherein the fifth temperature difference is a difference between the temperature measured by the fourth temperature sensor and the temperature measured by the first temperature sensor.

11. A method for measuring flow, comprising:
- determining an initial value of flow of a fluid passing through a temperature sensor part and a tube, wherein the temperature sensor part comprises first, second, third and fourth temperature sensors disposed sequentially along a flow direction of the fluid;
- supplying the fluid to the tube;
- recognizing the flow direction of the fluid passing through the tube, based on a temperature measured by the temperature sensor part;
- deciding an applied equation for measuring the flow of the fluid, based on the temperature measured by the temperature sensor part; and
- determining the flow based on the applied equation,
- wherein in the deciding the applied equation, the applied equation is decided based on a range of a first comparison value which is a difference between a first temperature difference and a second temperature difference,
- wherein the first temperature difference is a difference between the temperature measured by the fourth temperature sensor and the temperature measured by the second temperature sensor, and
- wherein the second temperature difference is a difference between the temperature measured by the second temperature sensor and the temperature measured by the first temperature sensor.

12. The method of claim 11, wherein the initial value of each of the first to fourth temperature sensors and the initial value of the flow of the fluid are determined to be zero.

13. The method of claim 12, wherein in the recognizing the flow direction of the fluid, the flow direction of the fluid is recognized by the temperature measured by the second and third temperature sensors respectively disposed at both sides of the heater.

14. The method of claim 11, wherein in the determining the flow, the flow is proportional to the first comparison value when the first comparison value is less than 10° C., and the flow has a logarithmic relationship with the first comparison value when the first comparison value is between 10° C. and 16° C.

15. The method of claim 11, wherein in the determining the flow, the flow has an exponential relationship with a second comparison value when the first comparison value is between 16° C. and 21° C.,
- wherein the second comparison is a difference between a third temperature difference and a fourth temperature difference,
- wherein the third temperature difference is a difference between the temperature measured by the fourth temperature sensor and the temperature measured by the third temperature sensor, and
- wherein the fourth temperature difference is a difference between the temperature measured by the third temperature sensor and the temperature measured by the first temperature sensor.

16. The method of claim 11, wherein in the determining the flow, the flow has a logarithmic relationship with a third comparison value when the first comparison value is over 21° C.,
- wherein the third comparison value is the sum of a fifth temperature difference and the second temperature difference, and
- wherein the fifth temperature difference is a difference between the temperature measured by the fourth temperature sensor and the temperature measured by the first temperature sensor.

* * * * *